(12) United States Patent
Tal

(10) Patent No.: US 7,722,567 B2
(45) Date of Patent: *May 25, 2010

(54) ACCESS DEVICE

(75) Inventor: Michael Tal, Woodbridge, CT (US)

(73) Assignee: Yale University, New Haven, CT (US)

( * ) Notice: Subject to any disclaimer, the term of this patent is extended or adjusted under 35 U.S.C. 154(b) by 832 days.

This patent is subject to a terminal disclaimer.

(21) Appl. No.: 11/275,292

(22) Filed: Dec. 21, 2005

(65) Prior Publication Data

US 2006/0129100 A1 Jun. 15, 2006

Related U.S. Application Data

(63) Continuation of application No. 10/329,173, filed on Dec. 24, 2002, now Pat. No. 7,025,746.

(60) Provisional application No. 60/343,814, filed on Dec. 26, 2001.

(51) Int. Cl.
*A61M 5/178* (2006.01)
(52) U.S. Cl. .................. 604/164.01; 604/164.1
(58) Field of Classification Search .............. 604/45, 604/158, 161, 164.01, 164.08–164.09, 164.11, 604/164.13, 900, 164.1
See application file for complete search history.

(56) References Cited

U.S. PATENT DOCUMENTS

| | | | |
|---|---|---|---|
| 3,539,034 A | 11/1970 | Tafeen | |
| 3,565,074 A | 2/1971 | Foti et al. | 128/214.4 |
| 3,995,628 A | 12/1976 | Gula et al. | |
| 4,068,659 A | 1/1978 | Moorehead | |
| 4,205,675 A | 6/1980 | Vaillancourt | |
| 4,411,655 A | 10/1983 | Schreck | |
| 4,417,886 A | 11/1983 | Frankhouser et al. | |
| 4,525,157 A | 6/1985 | Vaillancourt | 604/510 |
| 4,581,019 A | 4/1986 | Curelaru et al. | |
| 4,629,450 A | 12/1986 | Suzuki et al. | |
| 4,655,750 A | 4/1987 | Vaillancourt | |
| 4,772,264 A | 9/1988 | Cragg | |
| 4,791,937 A | 12/1988 | Wang | |
| 4,850,975 A | 7/1989 | Furukawa et al. | |
| 4,894,052 A | 1/1990 | Crawford | 604/507 |
| 4,944,728 A | 7/1990 | Carrell et al. | |
| 4,955,890 A | 9/1990 | Yamamoto et al. | |

(Continued)

FOREIGN PATENT DOCUMENTS

| | | |
|---|---|---|
| EP | 0139091 | 5/1985 |
| EP | 0161636 A2 | 11/1985 |
| EP | 0502714 | 9/1992 |
| EP | 0806221 A2 | 11/1997 |
| KR | 20050027359 | 3/2005 |
| WO | WO-2007/046850 | 4/2007 |

OTHER PUBLICATIONS

International Search Report for PCT Application No. PCT/US/2006/011624, mailed Oct. 17, 2007.

(Continued)

*Primary Examiner*—Nicholas D Lucchesi
*Assistant Examiner*—Theodore J Stigell
(74) *Attorney, Agent, or Firm*—Scott E. Kamholz; Foley Hoag LLP

(57) ABSTRACT

A device may include a hollow needle, a dilator mounted coaxially on the needle, and a sheath mounted coaxially on the dilator. The dilator may be slideably displaceable relative to the sheath.

37 Claims, 9 Drawing Sheets

U.S. PATENT DOCUMENTS

| | | | |
|---|---|---|---|
| 4,961,729 A | 10/1990 | Vaillancourt | 604/164 |
| 4,978,334 A | 12/1990 | Toye et al. | 604/51 |
| 4,995,866 A | 2/1991 | Amplatz et al. | |
| 5,066,284 A | 11/1991 | Mersch et al. | 604/168 |
| 5,098,392 A | 3/1992 | Fleischhacker et al. | |
| 5,108,374 A | 4/1992 | Lemieux | |
| 5,114,401 A | 5/1992 | Stuart et al. | 604/53 |
| 5,158,544 A | 10/1992 | Weinstein | |
| 5,171,218 A | 12/1992 | Fonger et al. | 604/164 |
| 5,242,410 A | 9/1993 | Melker | 604/164.1 |
| 5,242,427 A | 9/1993 | Bilweis | |
| 5,246,426 A | 9/1993 | Lewis et al. | |
| 5,250,038 A | 10/1993 | Melker et al. | |
| 5,295,969 A | 3/1994 | Fischell et al. | 604/168 |
| 5,295,970 A | 3/1994 | Clinton et al. | 604/168.01 |
| 5,306,253 A | 4/1994 | Brimhall | |
| 5,312,355 A | 5/1994 | Lee | |
| 5,328,480 A | 7/1994 | Melker et al. | |
| 5,330,433 A | 7/1994 | Fonger et al. | 604/164 |
| 5,336,191 A | 8/1994 | Davis et al. | |
| 5,342,315 A | 8/1994 | Rowe et al. | |
| 5,366,441 A | 11/1994 | Crawford | |
| 5,380,290 A | 1/1995 | Makower et al. | 604/164 |
| 5,391,178 A | 2/1995 | Yapor | 606/192 |
| 5,512,052 A | 4/1996 | Jesch | |
| 5,542,932 A | 8/1996 | Daugherty | |
| 5,676,689 A | 10/1997 | Kensey et al. | |
| 5,688,249 A | 11/1997 | Chang et al. | |
| 5,690,619 A | 11/1997 | Erskine | |
| 5,704,914 A * | 1/1998 | Stocking et al. | 604/164.07 |
| 5,712,229 A | 1/1998 | Hopkins et al. | |
| 5,728,132 A | 3/1998 | Van Tassel et al. | |
| 5,795,339 A | 8/1998 | Erskine | |
| 5,810,780 A | 9/1998 | Brimhall et al. | |
| 5,820,596 A | 10/1998 | Rosen et al. | |
| 5,827,202 A | 10/1998 | Miraki et al. | |
| 5,830,190 A | 11/1998 | Howell | 604/168 |
| 5,833,662 A | 11/1998 | Stevens | |
| 5,885,217 A | 3/1999 | Gisselberg et al. | |
| 5,885,253 A * | 3/1999 | Liu | 604/164.04 |
| 5,904,657 A | 5/1999 | Unsworth et al. | |
| 5,919,160 A | 7/1999 | Sanfilippo, II | |
| 5,935,110 A | 8/1999 | Brimhall | |
| 6,027,480 A | 2/2000 | Davis et al. | |
| 6,074,377 A | 6/2000 | Sanfilippo, II | |
| 6,080,141 A | 6/2000 | Castro et al. | |
| 6,120,494 A | 9/2000 | Jonkman | |
| 6,159,179 A | 12/2000 | Simonson | 604/117 |
| 6,179,813 B1 | 1/2001 | Ballow et al. | |
| 6,210,366 B1 | 4/2001 | Sanfilippo, II | |
| 6,277,100 B1 | 8/2001 | Raulerson et al. | 604/212 |
| 6,336,914 B1 | 1/2002 | Gillespie, III | |
| 6,436,070 B1 | 8/2002 | Botich et al. | |
| 6,461,362 B1 | 10/2002 | Halseth et al. | |
| 6,475,207 B1 | 11/2002 | Maginot et al. | 604/508 |
| 6,488,662 B2 | 12/2002 | Sirimanne | 604/164.01 |
| 6,500,152 B1 | 12/2002 | Illi | 604/164.07 |
| 6,524,277 B1 | 2/2003 | Chang | |
| 6,607,511 B2 | 8/2003 | Halseth et al. | 604/164.08 |
| 6,626,868 B1 | 9/2003 | Prestidge et al. | |
| 6,641,564 B1 | 11/2003 | Kraus | 604/164.1 |
| 6,692,462 B2 | 2/2004 | Mackenzie et al. | 604/104 |
| 6,692,482 B2 | 2/2004 | Heller et al. | 604/528 |
| 6,695,816 B2 | 2/2004 | Cassidy | |
| 6,726,659 B1 | 4/2004 | Stocking et al. | |
| 6,808,520 B1 | 10/2004 | Fourkas et al. | 604/526 |
| 6,836,687 B2 | 12/2004 | Kelley et al. | 607/122 |
| 6,905,481 B2 | 6/2005 | Sirimanne | 604/164.01 |
| 6,994,693 B2 | 2/2006 | Tal | |
| 7,001,396 B2 | 2/2006 | Glazier et al. | |
| 7,025,746 B2 | 4/2006 | Tal | |
| 2002/0072712 A1 | 6/2002 | Nool et al. | 604/167.01 |
| 2002/0087076 A1 | 7/2002 | Meguro et al. | |
| 2003/0032927 A1 | 2/2003 | Halseth et al. | 604/198 |
| 2003/0216771 A1 | 11/2003 | Osypka et al. | |
| 2004/0092879 A1 | 5/2004 | Kraus et al. | 604/158 |
| 2004/0171988 A1 | 9/2004 | Moretti | 604/158 |
| 2006/0015071 A1 | 1/2006 | Fitzgerald | |
| 2007/0282300 A1 | 12/2007 | Attawia et al. | |
| 2008/0262430 A1 | 10/2008 | Anderson et al. | |
| 2008/0262431 A1 | 10/2008 | Anderson et al. | |
| 2008/0294111 A1 | 11/2008 | Tal et al. | |

OTHER PUBLICATIONS

International Search Report for PCT Application No. PCT/US/2002/041371, mailed Oct. 2, 2003.

Examination Report for European Application No. 02806219.8-2310 dated Sep. 18, 2007.

Examination Report for European Application No. 02806219.8-2310 dated May 16, 2008.

International Search Report and Written Opinion for PCT Application No. PCT/US/2008/060914, mailed Mar. 17, 2009.

International Search Report and Written Opinion for PCT Application No. PCT/US2008/060930, mailed Mar. 11, 2009.

International Search Report for PCT Application No. PCT/US/2008/051950, mailed Oct. 22, 2008.

International Search Report for PCT/US2009/037204, mailed on Jun. 26, 2009.

Supplementary European Search Report for European Application No. 06 844 083.3-1526, mailed Mar. 3, 2009.

Photos of a peripheral emergency infusion device Applicant believes to be produced by Arrow International Inc.

Photos of an infusion device Applicant believes to be produced by B. Braun Medical Inc.

* cited by examiner

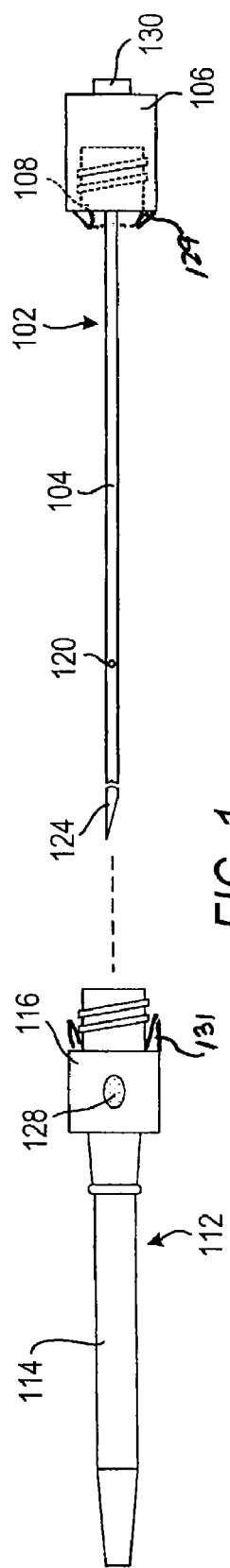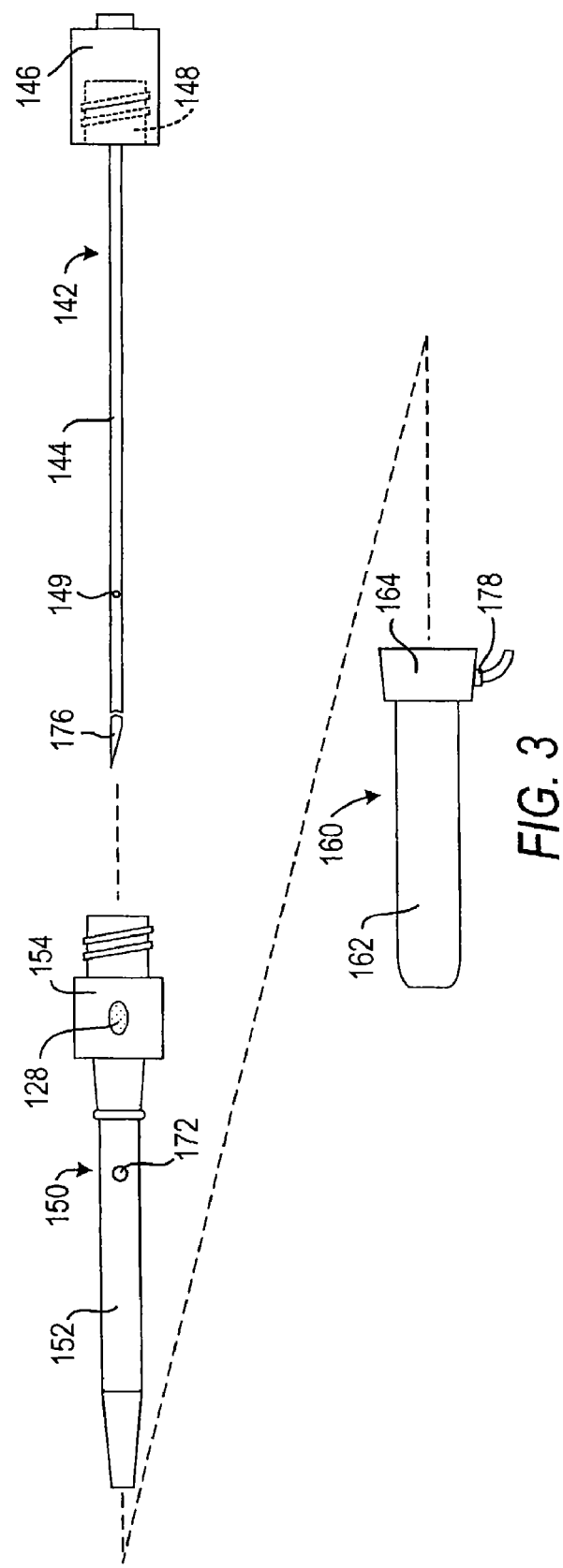
FIG. 1
FIG. 3

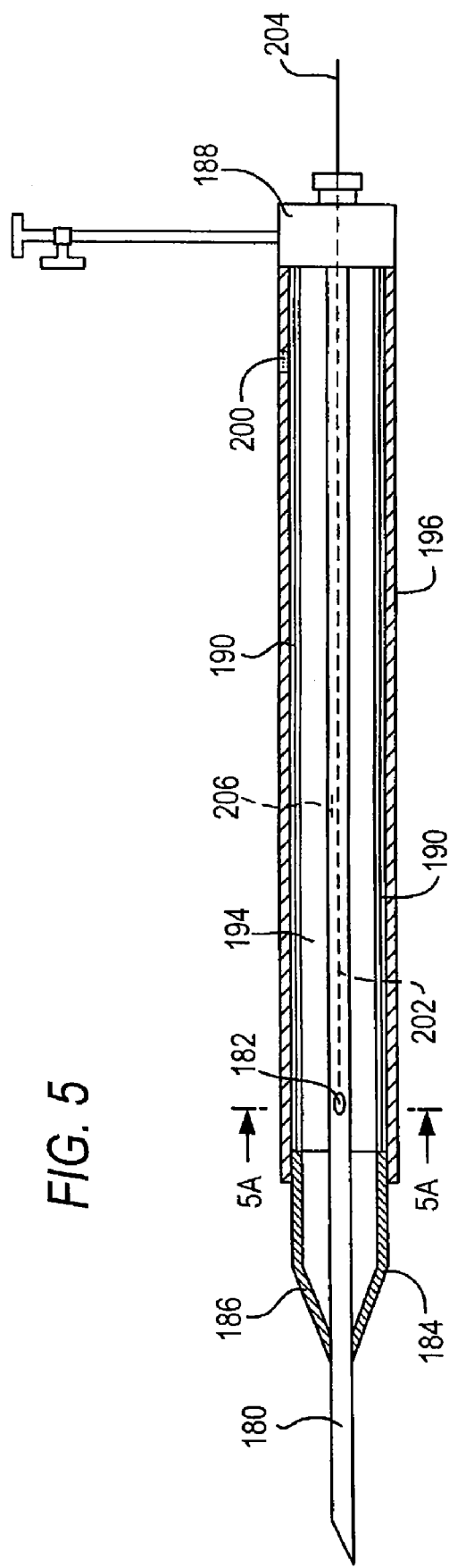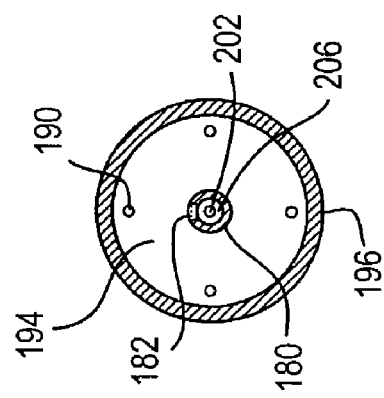
FIG. 5
FIG. 5A

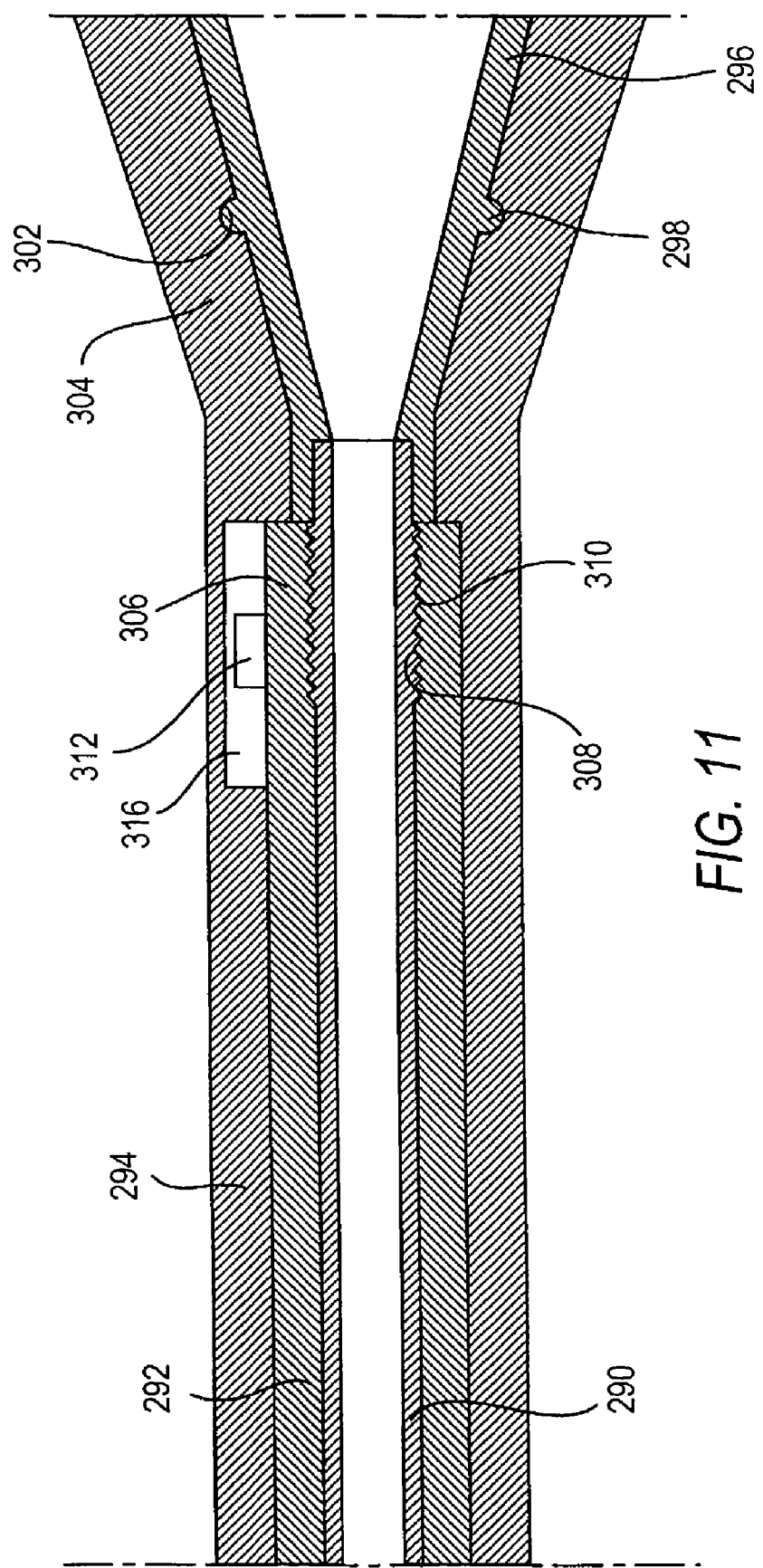

ACCESS DEVICE

CROSS-REFERENCE TO RELATED APPLICATIONS

This application is a continuation of U.S. application Ser. No. 10/329,173, filed Dec. 24, 2002, now U.S. Pat. No. 7,025,746, hereby incorporated herein by reference, which claims the benefit of U.S. Provisional Application No. 60/343,814, filed Dec. 26, 2001.

FIELD OF THE INVENTION

This invention is directed to vascular access. More particularly, this invention is directed to a vascular access device that is easier, safer, and faster to use than prior such devices.

BACKGROUND OF THE INVENTION

A preferred non-surgical method for inserting a catheter or vascular sheath into a blood vessel involves the use of the Seldinger technique, which includes an access needle that is inserted into a patient's blood vessel. A guidewire is inserted through the needle and into the vessel. The needle is removed, and a dilator and sheath combination are then inserted over the guidewire. The dilator and sheath combination is then inserted a short distance through the tissue into the vessel, after which the dilator is removed and discarded. The catheter is then inserted through the sheath into the vessel to a desired location. A number of vascular access devices are known. See, for example, U.S. Pat. Nos. 4,581,019, 4,629,450, 4,772,264, 4,978,334, 5,158,544, 5,424,410, 5,312,355, 5,512,052, 5,728,132, 5,885,217, 5,919,160, 6,120,494, 6,179,823, and 6,210,366, each of which is incorporated herein by reference, wherein various devices for vascular access are described. However, none of these devices has the ease and safety of use that physicians would prefer, and there is thus a need for an easier-to-use and safer vascular access device, especially one that would clearly indicate when a blood vessel has been punctured.

OBJECTS OF THE INVENTION

It is an object of the invention to provide vascular access.

It is also an object of the invention to provide easier, safer, and faster vascular access.

It is additionally an object of the invention to provide a vascular access device that eliminates the possibility of inadvertent guidewire misplacement into the vascular system during the vascular access procedure.

It is a further object of the invention to provide a method of introducing catheters or other medical devices in an easier, safer, and faster procedure, where the appearance of a patient's blood in the vascular access device indicates to the practitioner that the needle has accessed the desired vessel.

These and other objects of the invention will become more apparent in the discussion below.

SUMMARY OF THE INVENTION

According to the invention, a dilator or a sheath and dilator are mounted on a needle, which needle has a lateral opening proximal to the needle distal tip. Prior to insertion, the needle is positioned so that the distal end of the needle is distal to the distal end of the dilator. After insertion of the needle into a blood vessel, the needle opening permits blood to flow into an annular space in the dilator or between the needle and the dilator to indicate that the distal end of the needle has punctured the blood vessel. Additionally or alternatively, blood flows into an annular space formed by the sheath to indicate that the blood vessel has been punctured. In addition, blood may flow to an optional side port to provide further indication access has been achieved.

Once vascular access is achieved, that is, once the distal tip of the needle punctures a blood vessel and blood flows through a lateral opening in the needle to one of the annular spaces described above and as appropriate, into a side port, a guidewire is threaded through the needle, and then the entire apparatus, including the needle, the dilator, and a sheath, can be advanced over the guidewire into the blood vessel. At a desired time the sheath, needle, and dilator can be advanced over the guidewire. When the sheath is in position, the inner dilator, needle and guidewire can be removed together. Thus, the guidewire protects the needle tip, and the needle, with the guidewire in it, can then be bent for added safety, to prevent removal of the guidewire and consequential exposure of the needle tip. Alternatively, the guidewire can be left in place for catheter placement.

In one embodiment of the invention, the dilator has a distal member that can be advanced distally or the distal tip of the needle can be retracted so that the distal tip of the dilator distal member extends distally over the distal tip of the needle. The dilator distal member then protects the blood vessel wall as the needle, dilator or needle, dilator, sheath are advanced or withdrawn from a blood vessel, preferably over a guidewire. In addition, when the needle, dilator or needle, dilator, sheath are pulled out, the healthcare worker is protected.

In another embodiment of the invention, there is a coaxial dilator system, with an inner dilator and an outer dilator. The inner dilator can be advanced independently distally to the distal tip of the needle. The inner dilator then covers the needle tip, the inner dilator distal member then protects the blood vessel wall as the needle, dilator or the needle, dilator, sheath are advanced or withdrawn from a blood vessel, preferably over a guidewire. In addition, when the needle or needle, dilator, and/or sheath are pulled out, the worker is protected.

In another embodiment of the invention the needle can be rotated relative to the dilator or the dilator and sheath, so that the needle tip, which is inserted into a blood vessel with the needle distal tip bevel up, can be rotated 180° so that the needle distal tip bevel is down. When the needle distal tip is in this position, it is less likely that movement of the needle distal tip will cause injury to the blood vessel. The proximate portion of the needle member may have color coding, words, or other indicia to indicate the relative position of the needle tip level. Also, the needle member proximal portion may have a notch, pivot, indent, or other mechanism to indicate relative position and/or to hold the needle member in position relative to the dilator or the dilator and sheath.

The vascular access device of the invention has several uses, including access to every vessel when a vascular sheath is needed as in stent placement, Percutaneous Transluminal Coronary Angioplasty (PTCA), etc. or when a peel-away sheath is needed, for example, for inserting PICC lines, pacemaker leads, etc. In addition, the invention would be useful for access to dialysis grafts and fistulas, which are superficial structures and where access is sometimes needed quickly, especially during a de-clotting procedure. Another use would be for placement of central lines (subclavian or internal jugular). Instead of use of a large (18 G) needle (current technique), followed by advancement of a dilator over a guidewire and exchanging it for a triple lumen catheter or vascular sheath, according to the invention a large needle or a small needle can be used to gain vascular access with a vascular sheath through which a triple lumen or any other catheter can be safely placed.

The present invention has several advantages, the first of which is its efficiency. Instead of the current multi-step access method with an exchange of guidewires and sheaths, this invention reduces the number of steps and simplifies access. Another advantage is safety. After a vessel is accessed, the guidewire can be left in to protect the needle tip. The needle, dilator and guidewire can be removed together after the sheath is in place. If no additional access is needed in the same procedure, the needle can be bent for added safety. This is contrary to the current technique where the unprotected bloody needle is removed from the guidewire after vascular access is gained. Alternatively, the guidewire can be left in place to provide further access through the sheath and the dilator distal member protects the distal tip of the needle and ultimately the user. Another advantage is the reduction of infection. By minimizing the number of guidewires and sheaths necessary to obtain vascular access, the opportunities for inadvertent contamination are decreased. A further advantage is that under non-hospital or field conditions, use of the invention will decrease the possibility of infection due to a non-sterile environment. A yet further advantage is the added stiffness of the system. The added stiffness provided by the needle is enabling advancement of the system without multiple dilatations and reduced trauma to the patient.

An even further advantage relates to the bleeding from the needle, the dilator, and around the wires that occurs during guidewire exchanges with current techniques. Such bleeding increases the spread of blood over the surgical field and the operator's gloves, thereby, increasing the chance of infection in case an inadvertent needle stick happens. The device of the invention will decrease this risk of infection because the blood will flow into the sheath rather than into the surgical field as in the current technique.

Another and further advantage of one embodiment of the invention, is that there is no need for over-the-wire exchanges. The device can be configured to eliminate the possibility of inadvertent guidewire misplacement into the vascular system during the access procedure. In the current technique, with exchange of the needle for a dilator and then for the sheath, it is a known complication that the operator fails to grasp the guidewire during those exchanges and the guidewire is inadvertently advanced with the dilator or catheter into the patient's vascular system. The guidewire then has to be removed either surgically or snared percutaneously.

Lastly, the present invention will be cost-effective. The system of the invention will eliminate the need for an additional guidewire and coaxial dilator to be used in gaining vascular access.

BRIEF DESCRIPTION OF THE DRAWINGS

FIGS. 1 and 2 are each a schematic representation of one embodiment of the invention;

FIGS. 3 and 4 are each a schematic representation of another embodiment of the invention;

FIG. 5 is a partly cross-sectional view of a further embodiment of the invention;

FIG. 5A is a cross-section along line 5a-5a;

FIG. 11 is a schematic cross-sectional view of the proximal portion of the system of FIGS. 10A and 10B.

DETAILED DESCRIPTION OF THE INVENTION

Figure 2:
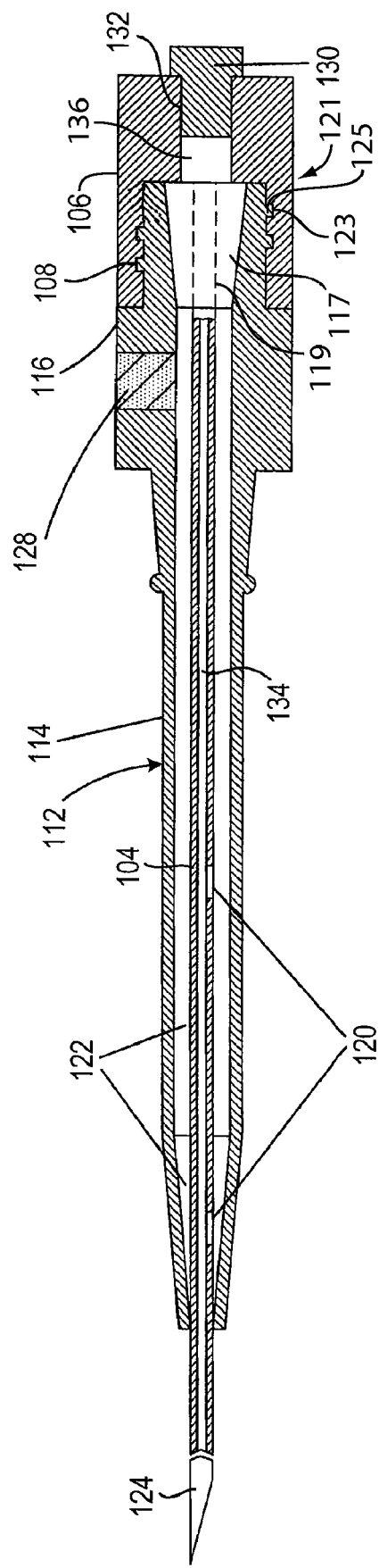

The invention can perhaps be better appreciated from the drawings. In FIGS. 1 and 2 a needle section 102 comprises a needle 104 and a proximal portion 106 with a twist lock member 108, and a dilator section 112 comprises a dilator 114 and a hub 116. In a preferred embodiment of the invention, needle 104 has one or more openings 120. Dilator 114 is preferably clear, semi-opaque, or translucent so that when blood flows into needle 104 and then through an opening 120 either (1) into an annular space 122 between needle 104 and dilator 114 or (2) into or through spaces (not shown) in dilator 114, the physician can see the blood. This will indicate to the physician that the distal end 124 of needle 104 has punctured a blood vessel (not shown).

As can be seen in FIG. 2, dilator hub 116 releasably engages needle proximal section 106. Here, dilator hub 116 comprises a conical recess 117 that receives a member 119 forming a part of needle proximal section 106. Needle proximal section 106 comprises an annular portion 121 having threading 123 that engages reciprocal threading 125 on hub 116. Other arrangements of threading, detents, or other snap- or force-fit configurations that achieve the same purpose of releasably engaging the proximal portions of the needle and dilator sections are also within the scope of the invention.

Hub 116 may optionally have a porous vent 128. Needle proximal portion 106 may optionally have a porous vent plug 130 that fits a channel 132 in fluid communication with lumen 134 of needle 104, recess 117, and needle proximal portion 106 having lumen 136.

Needle proximal portion 106 may have color coding, words, or other indicia, such as a pivot or notch, to indicate to the operator the position of the bevel of distal tip 124 relative to dilator 114. Also, there may be a mechanical fit between dilator 114 and needle 104 so that the operator would sense by feel or sound when the needle has been rotated to change the position of the needle tip bevel.

Figure 4:
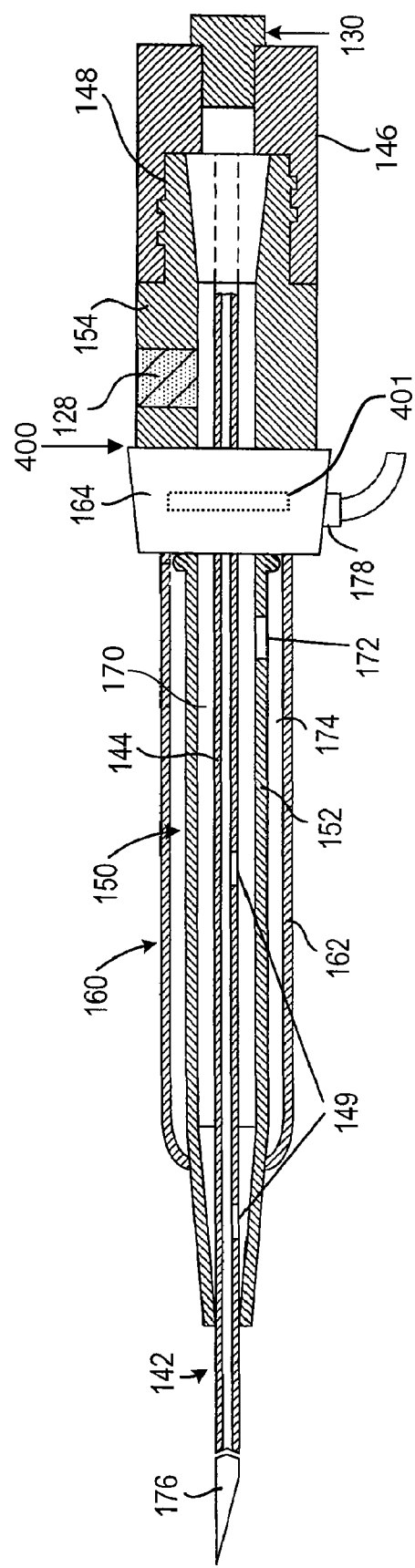

In the embodiment of the invention shown in FIGS. 3 and 4, a needle section 142 comprises a needle 144 and a proximal portion 146 with a twist lock member 148, a dilator section 150 comprises a dilator 152 and a hub 154, and a sheath section 160 comprises a sheath 162 and a proximal portion 164. In a preferred embodiment of the invention, needle 144 has one or more openings 149. Dilator 152 and sheath 162 are preferably clear, semi-opaque, or translucent so that when blood flows into needle 144 and then through opening 149 (1) into an annular space 170 between needle 144 and dilator 152, (2) into or through spaces (not shown) in dilator 152, or (3) through an opening 172 into an annular space 174 between dilator 152 and sheath 162, the physician can see the blood. As above, this will indicate to the physician that the distal end 176 of needle 144 has punctured a blood vessel (not shown). Preferably sheath proximal portion 164 has a port 178 so that blood can be aspirated through a syringe (not shown). The sheath may contain a hemostatic valve 401 in the proximal end 164 to prevent blood flow out the proximal end of the sheath.

Proximal sections 106 and 116 and 146 and 154, respectively, may optionally have luer connecting members. For example, section 108 may have a male luer lock 129, and section 116 may have a female luer connector 131. Sections 146 and 154 may have comparable members, respectively.

As shown in FIG. 4 sections 142, 150, and 160 can be inserted into one another. Proximal sections 146, 154, 164 can twist or snuggly fit together, such as with a luer connector, threading, a pressure or snap fit, a detent/groove arrangement, or a combination thereof. The snug fit can form a seal 400, for example between the sheath and dilator. The structure shown in FIG. 2 is especially applicable here.

In another embodiment of the invention as shown in a partial cross-section in FIG. 5, needle 180 has an opening or side hole 182. Dilator 184, which is arranged coaxially to needle 180, has a substantially hollow distal section 186 and a substantially solid proximal section 188, which sections 186 and 188 are connected by rigid or substantially rigid longitudinal members 190, to form an interrupted or discontinuous structure. The space between sections 186 and 188 not occupied by members 190 constitutes an annular or substantially annular space 194, into which blood can flow from opening 182. Sheath 196 is transparent or translucent, so that the blood in space 194 can be observed by the physician.

Preferably dilator 184 has one or more small openings, pores, or porous material 200, for example, in sheath 196, to allow air or gas to leave annular space 194 as blood enters. The openings themselves, or the openings in the porous material, are small enough that air will escape but blood will be retained. Suitable porous materials include a porous polymer such as self-sealing, white porous HDPE of pore size 2.5 microns.

The distal end 202 of a guidewire 204 is preferably preloaded, that is, positioned within a lumen 206 of needle 180. In this way blood will flow into needle 180 and out through opening 182, and not proximally out lumen 206. Once the physician sees the blood in annular space 194, guidewire 204 can be advanced distally through lumen 206 into a blood vessel (not shown). Another view of the relationship between needle 180, dilator longitudinal members 190, and sheath 196 can be seen in the cross-sectional view shown in FIG. 5A.

Figure 6:
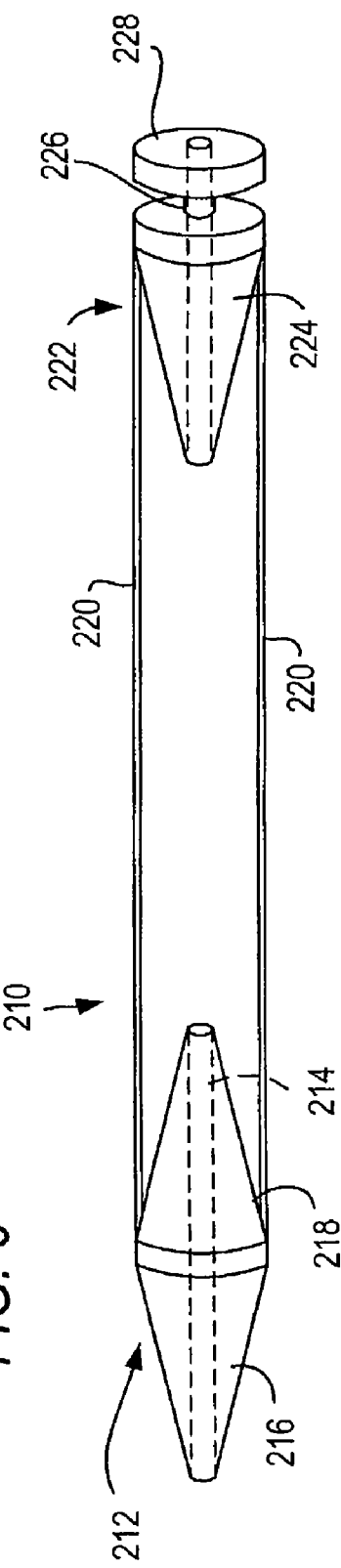
FIG. 6 is a partly cross-sectional view of another aspect of the invention.
Figure 7:
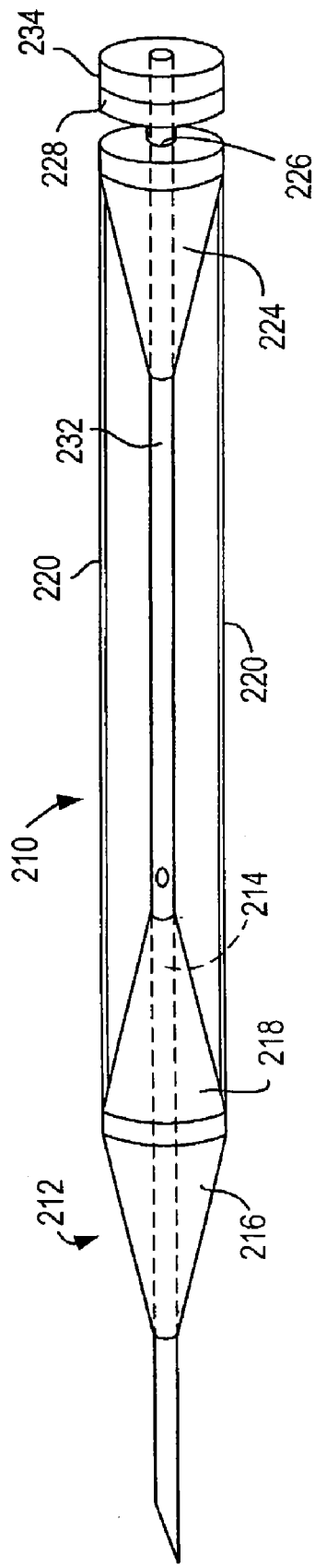
FIG. 7 is a partly cross-sectional view of a further aspect of the invention.

Separate designs for a dilator member according to the invention are shown in more detail in FIGS. 6 and 7. In FIG. 6, a dilator 210 shown has conical elements. A distal dilation section 212 comprises a double cone design with a passageway 214 extending from the tip of one conical element 216 to the tip of another conical element 218. At least two stabilizing longitudinal members 220 extend from distal section 212 to a proximal section 222, which preferably comprises a single conical element 224 with a passageway 226 and a proximal twist or locking section 228.

The embodiment of the invention shown in FIG. 7 comprises a dilator-needle combination where the dilator device described in FIG. 6 also comprises a needle 232 that extends through passageway 214 to and through passageway 226. Needle 232 has a proximal section 234 that comprises a twist or locking arrangement.

Figure 8:
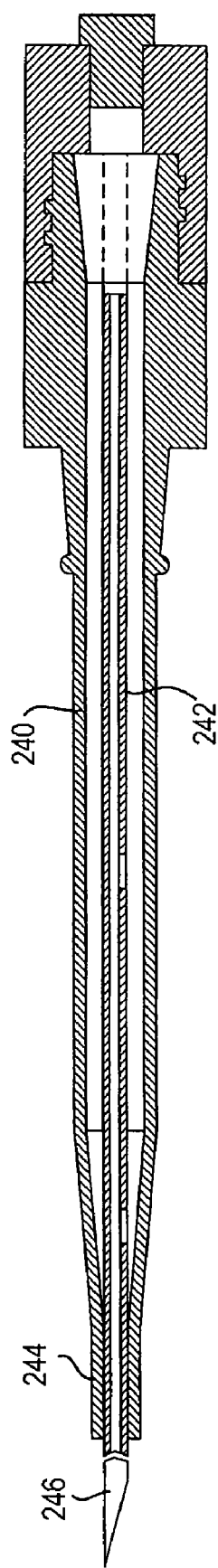
FIG. 8 is a partly cross-sectional view of an embodiment of the invention where the distal portion of the dilator extends distally.
Figure 9A:
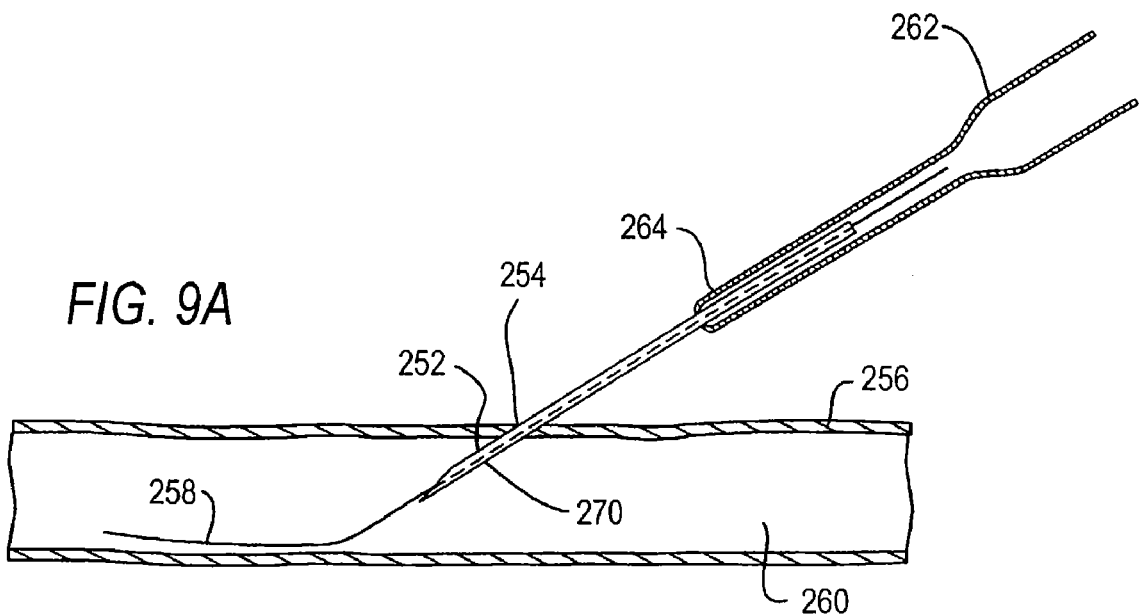
FIGS. 9A to 9C are schematic representations of use of the embodiment of the invention shown in FIG. 8.
Figure 9B:
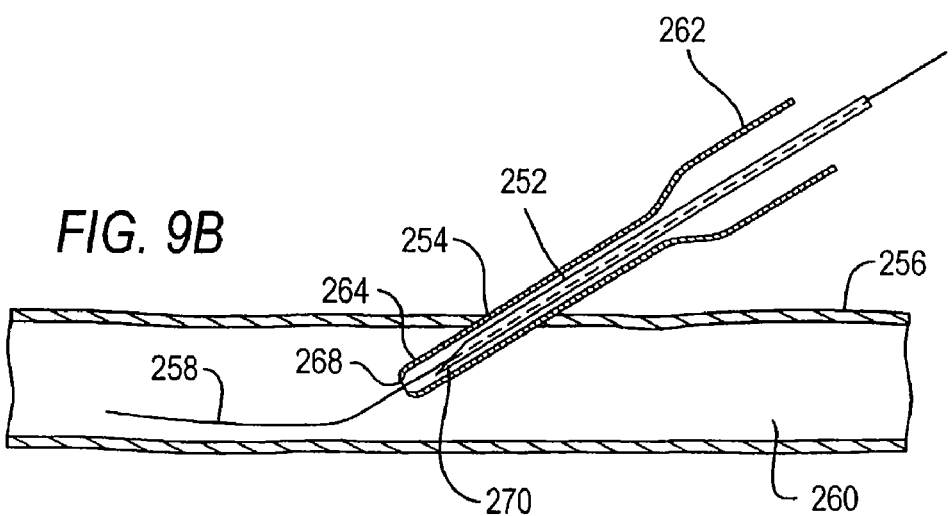
Figure 9C:
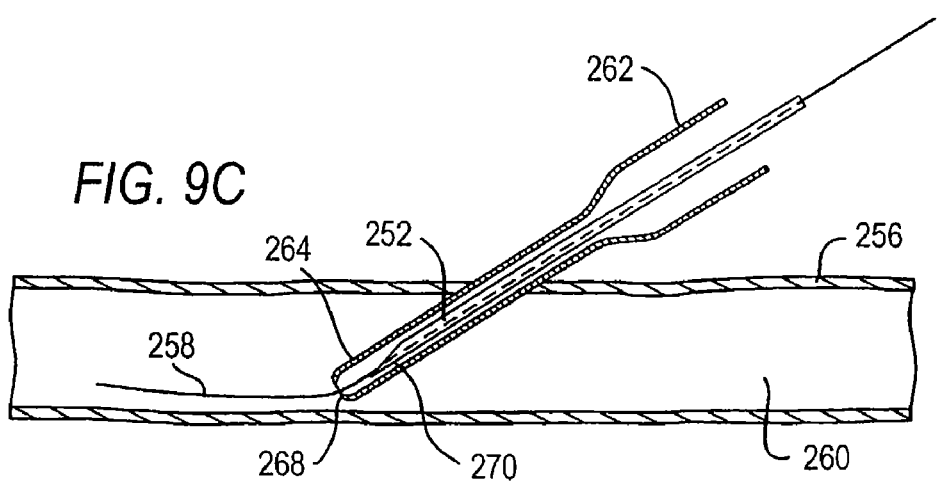

In the partial representation of an embodiment of the invention shown in FIG. 8, a dilator 240 is arranged circumferentially around a needle 242. Dilator 240 has a distal portion 244 that extends distally toward the distal tip 246 of needle 242. Alternatively, the inner, elongated dilator is coaxially located within the larger outer dilator. The inner elongated member can be advanced over the needle to protect the tip. As depicted in FIGS. 9A to 9C, a needle 252 is positioned in a puncture opening 254 in a blood vessel 256. A guidewire 258 extends distally from needle 252 into a lumen 260 of blood vessel 256.

A dilator 262 positioned circumferentially around needle 252 has a distal portion 264. As shown in FIG. 9B, dilator distal portion 264 can be advanced over needle 252 so that the distal tip 268 of dilator distal portion 264 extends distally of the distal tip 270 of needle 252. Then, when, as shown in FIG. 9C, needle 252 and dilator 262 are advanced distally over guidewire 258, needle distal tip 270 is protected by dilator distal portion 264.

Figure 10A:
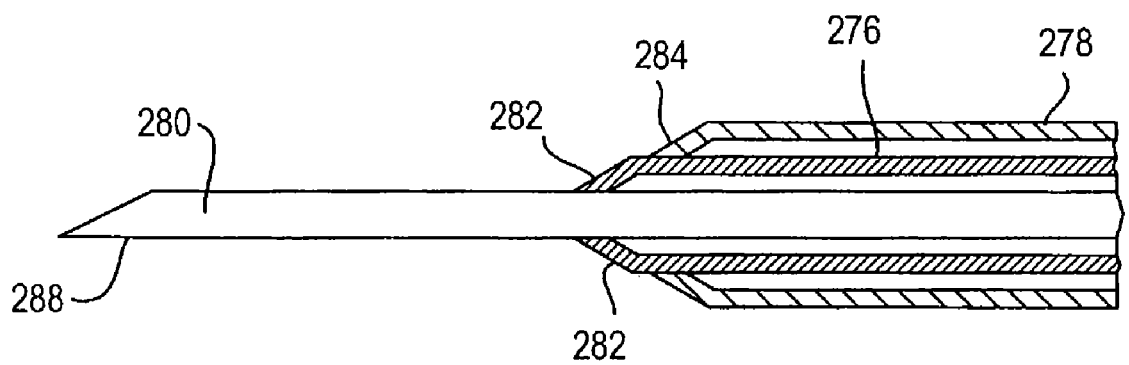
FIGS. 10A and 10B are schematic representations of an embodiment of the invention with a coaxial dilator system.
Figure 10B:
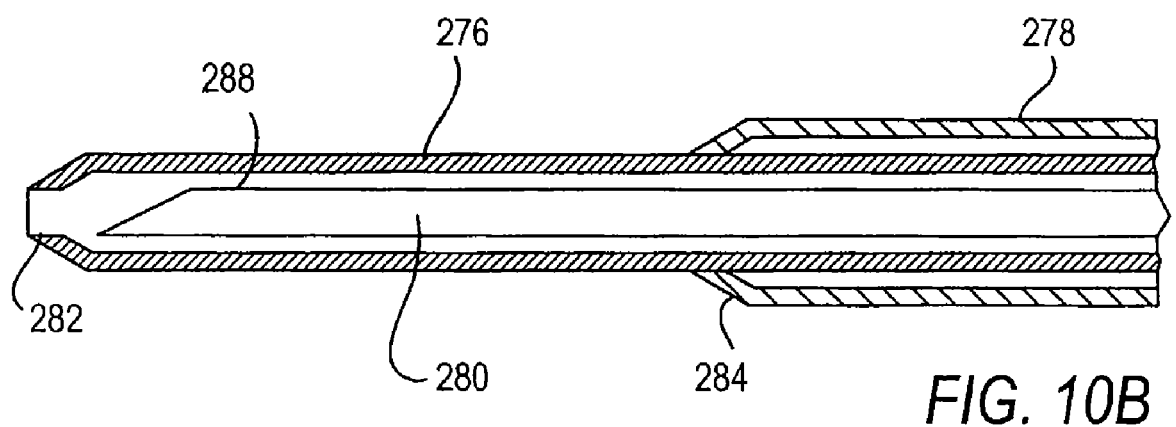

The embodiment of the invention shown in FIGS. 10A and 10B comprises a coaxial dilator system comprising inner dilator 276 and outer dilator 278. Dilators 276 and 278 are arranged around needle 280, and the distal end 282 of inner dilator 276 is initially slightly distal of the distal end 284 of outer dilator 278. The proximal end (not shown) of inner dilator 276 is advanced distally to cause inner dilator distal end 282 to cover the distal end 288 of needle 280. Preferably dilators 276 and 278 interact or are held so that they retain their relative positions with regard to each other and needle 280 as the needle, dilator or needle, dilator, sheath combination is advanced into or withdrawn from a blood vessel (not shown), optimally over a guidewire (not shown).

The coaxial dilator system shown in FIGS. 10A and 10B requires an activation system that causes one dilator to move in relation to the other dilator. It is preferred that the inner dilator would be advanced distally to cover the distal end of the needle while the outer dilator remains constant, or in place. Preferably the dilator system would be configured so that the outer dilator would remain relatively, substantially in place while the inner dilator is pushed, pulled, or slid in the distal direction. In the embodiment shown in FIG. 11, a proximal needle section 290 is circumferentially surrounded by a proximal inner dilator section 292 and an outer dilator section 294. Tapered needle hub 296 has at least one annular projection or ring 298 that is received in an annular groove 302 in the tapered outer dilator proximal hub 304. Inner dilator hub 306 has threading 308 that engages reciprocal threading 310 on needle 290 or on a separate needle member attached to needle 290 or needle hub 296. Inner dilator hub 306 has a projection or wing 312 that moves within, and is guided by, a slot 316 that prevents rotation of inner dilator 292 with respect to outer dilator 294. It is within the scope of the invention that other mechanical arrangements known or discernible to those skilled in the art would be acceptable, so long as they permitted advancement of the distal portion of the inner dilator over the distal portion of the needle without rotation of the inner dilator relative to the outer dilator.

The invention herein is comprised of conventional, physiologically acceptable materials. For example, the needle consists of a rigid polymer or a metal such as stainless steel, nitinol, or the like. The other elements will typically consist of suitable polymeric materials, such as polyethylene, polypropylene, fluoropolymers and copolymers such as perfluoro (ethylene-propylene) copolymer, polyurethane polymers or co-polymers.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A preassembled device for accessing a body space, the device comprising:
    a hollow needle having a sharpened distal tip and defining at least one side hole proximal to the distal tip;
    a dilator section comprising a dilator coaxially mounted on the needle; and
    a sheath section comprising a sheath coaxially mounted on the dilator,
    wherein at least one space capable of receiving body fluid occurs between an exterior of the sheath and an exterior of the needle that is visible from outside the sheath to confirm proper placement of the needle in a body space, and wherein at least one of the dilator section and sheath section has an opening allowing air egress from the space but inhibiting body fluid egress from the space.

2. The device of claim 1, wherein the dilator comprises a side fenestration that communicates with the side hole of the needle.

3. The device of claim 2, wherein the side fenestration communicates with the side hole via a second space defined between the exterior of the needle and the dilator.

4. The device of claim 2, wherein the space is defined between the dilator and the sheath and is in communication with the side fenestration.

5. The device of claim 4 additionally comprising a second space in communication with the side fenestration and the needle side hole, the second space being defined between the exterior of the needle and an interior of the dilator.

6. The device of claim 1, wherein the space is defined between the exterior of the needle and an interior of the dilator and communicates with the side hole in the needle.

7. The device of claim 6, wherein the opening is defined in the sheath section.

8. The device of claim 1, wherein the sheath is a peel-away sheath.

9. The device of claim 1, wherein the sheath comprises a catheter.

10. The device of claim 9, wherein the catheter is a multi-lumen catheter.

11. The device of claim 1, wherein the dilator and sheath are slideably displaceable together over the needle.

12. The device of claim 1, wherein the dilator is slideably displaceable over the needle at least to a position in which it covers a sharpened distal tip of the needle, thereby protecting it.

13. The device of claim 1, wherein the dilator is at least partially clear, semi-opaque, or translucent.

14. The device of claim 1, wherein the sheath is at least partially clear, semi-opaque, or translucent.

15. The device of claim 1, wherein the dilator comprises a discontinuous structure having a solid distal section connected to a solid proximal section by at least one longitudinal member, so that the at least one space is defined between the sheath and the needle and the space communicates with the hollow needle bore through the needle side hole.

16. The device of claim 1, wherein the dilator comprises a continuous tubular structure.

17. The device of claim 1, wherein the sheath section comprises a side port.

18. The device of claim 1, where the hollow needle has a length sufficient to reach a central blood vessel of a patient.

19. The device of claim 1, wherein the hollow needle has sufficient stiffness to support the dilator and sheath during advancement of the device into the blood vessel.

20. The device of claim 1, wherein the dilator comprises a distal dilation section having a double cone configuration.

21. The device of claim 1, further comprising a seal between the dilator and sheath.

22. The device of claim 1, wherein the needle is attached to a proximal needle hub, the dilator is attached to a proximal dilator hub, and the needle hub and dilator hub are interlockable with one another.

23. The device of claim 1, wherein the dilator section further comprises a proximal dilator hub attached to the dilator, the sheath section further comprises a proximal sheath hub attached to the sheath, and the dilator hub and sheath hub are interlockable with one another.

24. The device of claim 1, wherein the dilator section comprises a dilator hub and the sheath section comprises a sheath hub.

25. The device of claim 24, wherein the opening comprises a hole.

26. The device of claim 24, wherein the opening is entirely formed in the dilator hub.

27. The device of claim 24, wherein the sheath hub comprises a hemostatic valve.

28. The device of claim 1, wherein the opening is formed by a porous material.

29. The device of claim 1, further comprising a guidewire preloaded in the needle.

30. The device of claim 29, wherein the dilator and sheath are slideably displaceable together over the guidewire.

31. The device of claim 29, wherein a distal end of the guidewire is preloaded in the needle.

32. The device of claim 31, wherein the distal end is preloaded so as to lie behind the needle hole.

33. A preassembled device for accessing a body space, the device comprising:
  a hollow needle having a distal tip and defining at least one side hole proximal of the distal tip;
  a dilator section comprising a dilator disposed about at least a portion of the needle so as to define a first space between the needle and the dilator, the dilator having at least one side fenestration; and
  a sheath section comprising a sheath disposed about at least a portion of the dilator so as to define a second space, the second space communicating with the side fenestration such that a fluid path is defined through from an interior of the needle to the second space, the sheath section further having at least one opening to allow the egress of air while the body fluid flows into the second space through the side fenestration, the opening being configured to inhibit the passage of body fluid therethrough.

34. The device of claim 33, wherein the dilator has a tubular configuration and a distal portion of the dilator has a cross-sectional size larger than a portion of the dilator disposed proximally of the distal portion.

35. The device of claim 33 additionally comprising a guidewire slideable at least partially through the needle.

36. A preassembled device for accessing a body space, the device comprising:
  a hollow needle having a sharpened distal tip and at least one side hole disposed proximal of the tip;
  a dilator coaxially mounted on the needle;
  a sheath coaxially mounted on the dilator, at least one space capable of receiving body fluid being defined between an exterior of the sheath and an exterior of the needle, the space being visible from outside the sheath; and
  means for enhancing the uptake of body fluid into the space so as to confirm the proper placement of the distal tip of the needle in a body space, wherein the space is defined between the dilator and the sheath with the dilator having at least one side fenestration communicating with the side hole in the needle.

37. A preassembled device for accessing a body space, the device comprising:
  a hollow needle having a sharpened distal tip and at least one side hole disposed proximal of the tip;
  a dilator coaxially mounted on the needle;
  a sheath coaxially mounted on the dilator, at least one space capable of receiving body fluid being defined between an exterior of the sheath and an exterior of the needle, the space being visible from outside the sheath; and
  means for enhancing the uptake of body fluid into the space so as to confirm the proper placement of the distal tip of the needle in a body space, wherein said means for enhancing the uptake of body fluid is disposed on the sheath section.

* * * * *